United States Patent
Conklin

(10) Patent No.: US 10,849,752 B2
(45) Date of Patent: *Dec. 1, 2020

(54) METHODS FOR ANCHORING A DEVICE AT A NATIVE HEART VALVE ANNULUS

(71) Applicant: Edwards Lifesciences Corporation, Irvine, CA (US)

(72) Inventor: Brian S. Conklin, Orange, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 90 days.

This patent is subject to a terminal disclaimer.

(21) Appl. No.: 16/297,187

(22) Filed: Mar. 8, 2019

(65) Prior Publication Data

US 2019/0201200 A1 Jul. 4, 2019

Related U.S. Application Data

(60) Continuation of application No. 15/482,529, filed on Apr. 7, 2017, now Pat. No. 10,238,489, which is a
(Continued)

(51) Int. Cl.
*A61F 2/24* (2006.01)
*A61F 2/02* (2006.01)

(52) U.S. Cl.
CPC .............. *A61F 2/2445* (2013.01); *A61F 2/02* (2013.01); *A61F 2/24* (2013.01); *A61F 2/2409* (2013.01); *A61F 2/2418* (2013.01); *A61F 2/2442* (2013.01); *A61F 2/2463* (2013.01); *A61F 2/2457* (2013.01); *A61F 2220/0008* (2013.01);
(Continued)

(58) Field of Classification Search
CPC .... A61F 2/2445; A61F 2/2442; A61F 2/2409; A61F 2/2454; A61F 2/2418; A61F 2/2463
See application file for complete search history.

(56) References Cited

U.S. PATENT DOCUMENTS

| 3,143,742 A | 8/1964 | Cromie |
| 3,320,972 A | 5/1967 | High et al. |
(Continued)

FOREIGN PATENT DOCUMENTS

| CN | 2356656 Y | 1/2000 |
| DE | 19532846 A1 | 3/1997 |
(Continued)

OTHER PUBLICATIONS

Krakow, "3F Therapeutics, Inc. Announces the First Clinical Implantation of the 3F Enable Aortic Heart Valve.TM., a Patented, Sutureless Implantation, Replacement Heart Valve Intended to Save Valuable Surgery Time and Reduce Time RelatedCornplications . . . " Healthcare Sales & Marketing Network News Feed, Jan. 18, 2005, pp. 1-2.
(Continued)

*Primary Examiner* — Dinah Baria
(74) *Attorney, Agent, or Firm* — Guy Cumberbatch

(57) ABSTRACT

A method and device for anchoring a prosthetic heart valve or annuloplasty ring to a valve annulus in a heart and a method of implanting same is disclosed. The device can include a prosthetic valve or annuloplasty ring with one or more anchors configured to be threaded or otherwise passed underneath a native leaflet and/or subvalvular tissue to secure the device at the native annulus.

20 Claims, 8 Drawing Sheets

Related U.S. Application Data continuation of application No. 14/797,163, filed on Jul. 12, 2015, now Pat. No. 9,737,401, which is a division of application No. 13/675,801, filed on Nov. 13, 2012, now Pat. No. 9,078,747.

(60) Provisional application No. 61/578,758, filed on Dec. 21, 2011.

(52) U.S. Cl.
CPC ............ A61F 2230/0054 (2013.01); A61F 2230/0069 (2013.01); A61F 2250/0018 (2013.01)

(56) References Cited

U.S. PATENT DOCUMENTS

| | | |
|---|---|---|
| 3,371,352 A | 3/1968 | Siposs et al. |
| 3,409,013 A | 11/1968 | Berry |
| 3,546,710 A | 12/1970 | Shumakov et al. |
| 3,574,865 A | 4/1971 | Hamaker |
| 3,628,535 A | 12/1971 | Ostrowsky et al. |
| 3,657,744 A | 4/1972 | Ersek |
| 3,686,740 A | 8/1972 | Shiley |
| 3,755,823 A | 9/1973 | Hancock |
| 3,839,741 A | 10/1974 | Haller |
| 4,035,849 A | 7/1977 | Angell et al. |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| RE30,912 E | 4/1982 | Hancock |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,702,250 A | 10/1987 | Ovil et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,865,600 A | 9/1989 | Carpentier et al. |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,041,130 A | 8/1991 | Cosgrove et al. |
| 5,059,177 A | 10/1991 | Towne et al. |
| 5,147,391 A | 9/1992 | Lane |
| 5,163,955 A | 11/1992 | Love et al. |
| 5,258,023 A | 11/1993 | Reger |
| 5,290,300 A | 3/1994 | Cosgrove et al. |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,444 A | 11/1994 | Kusuhara |
| 5,370,685 A | 12/1994 | Stevens |
| 5,376,112 A | 12/1994 | Duran |
| 5,396,887 A | 3/1995 | Imran |
| 5,397,351 A | 3/1995 | Pavcnik et al. |
| 5,411,522 A | 5/1995 | Trott |
| 5,411,552 A | 5/1995 | Andersen et al. |
| 5,413,676 A | 5/1995 | Nguyen et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,476,510 A | 12/1995 | Eberhardt et al. |
| 5,488,789 A | 2/1996 | Religa et al. |
| 5,489,297 A | 2/1996 | Duran |
| 5,489,298 A | 2/1996 | Love et al. |
| 5,500,016 A | 3/1996 | Fisher |
| 5,522,884 A | 6/1996 | Wright |
| 5,531,785 A | 7/1996 | Love et al. |
| 5,533,515 A | 7/1996 | Coller et al. |
| 5,549,665 A | 8/1996 | Vesely et al. |
| 5,554,185 A | 9/1996 | Block et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,776,188 A | 7/1998 | Shepherd et al. |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,865,801 A | 2/1999 | Houser |
| 5,885,228 A | 3/1999 | Rosenman et al. |
| 5,891,160 A | 4/1999 | Williamson, IV et al. |
| 5,895,420 A | 4/1999 | Mirsch, II et al. |
| 5,902,308 A | 5/1999 | Murphy |
| 5,904,695 A | 5/1999 | Krueger |
| 5,908,450 A | 6/1999 | Gross et al. |
| 5,919,147 A | 7/1999 | Jain |
| 5,921,934 A | 7/1999 | Ten |
| 5,921,935 A | 7/1999 | Hickey |
| 5,924,984 A | 7/1999 | Rao |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,607 A | 3/2000 | Williamson, IV et al. |
| 6,059,827 A | 5/2000 | Fenton, Jr. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |

(56) References Cited

U.S. PATENT DOCUMENTS

| | | |
|---|---|---|
| 6,110,200 A | 8/2000 | Hinnenkamp |
| 6,117,091 A | 9/2000 | Young et al. |
| 6,162,233 A | 12/2000 | Williamson, IV et al. |
| 6,168,614 B1 | 1/2001 | Andersen et al. |
| 6,176,877 B1 | 1/2001 | Buchanan et al. |
| 6,197,054 B1 | 3/2001 | Hamblin, Jr. et al. |
| 6,217,611 B1 | 4/2001 | Klostermeyer |
| 6,231,561 B1 | 5/2001 | Frazier et al. |
| 6,241,765 B1 | 6/2001 | Griffin et al. |
| 6,245,102 B1 | 6/2001 | Jayaraman |
| 6,283,127 B1 | 9/2001 | Sterman et al. |
| 6,287,339 B1 | 9/2001 | Vazquez et al. |
| 6,290,674 B1 | 9/2001 | Roue et al. |
| 6,312,447 B1 | 11/2001 | Grimes |
| 6,312,465 B1 | 11/2001 | Griffin et al. |
| 6,328,727 B1 | 12/2001 | Frazier et al. |
| 6,350,282 B1 | 2/2002 | Eberhardt |
| 6,371,963 B1 | 4/2002 | Lane |
| 6,402,780 B2 | 6/2002 | Williamson, IV et al. |
| 6,419,696 B1 | 7/2002 | Ortiz et al. |
| 6,425,916 B1 | 7/2002 | Garrison et al. |
| 6,432,134 B1 | 8/2002 | Anson et al. |
| 6,440,164 B1 | 8/2002 | Di Mateo et al. |
| 6,454,799 B1 | 9/2002 | Schreck |
| 6,458,100 B2 | 10/2002 | Roue et al. |
| 6,458,153 B1 | 10/2002 | Bailey et al. |
| 6,468,305 B1 | 10/2002 | Otte |
| 6,527,979 B2 | 3/2003 | Constantz et al. |
| 6,530,952 B2 | 3/2003 | Vesely |
| 6,558,416 B2 | 5/2003 | Cosgrove et al. |
| 6,558,429 B2 | 5/2003 | Taylor |
| 6,569,196 B1 | 5/2003 | Vesely |
| 6,582,462 B1 | 6/2003 | Andersen et al. |
| 6,585,766 B1 | 7/2003 | Huynh et al. |
| 6,652,578 B2 | 11/2003 | Bailey et al. |
| 6,682,559 B2 | 1/2004 | Myers et al. |
| 6,685,739 B2 | 2/2004 | DiMatteo et al. |
| 6,702,825 B2 | 3/2004 | Frazier et al. |
| 6,712,804 B2 | 3/2004 | Roue et al. |
| 6,719,789 B2 | 4/2004 | Cox |
| 6,730,118 B2 | 5/2004 | Spenser et al. |
| 6,730,121 B2 | 5/2004 | Oiliz et al. |
| 6,733,525 B2 | 5/2004 | Yang et al. |
| 6,746,472 B2 | 6/2004 | Frazier et al. |
| 6,764,508 B1 | 7/2004 | Roehe et al. |
| 6,767,362 B2 | 7/2004 | Schreck |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,797,002 B2 | 9/2004 | Spence et al. |
| 6,805,711 B2 | 10/2004 | Quijano et al. |
| 6,846,325 B2 | 1/2005 | Liddicoat |
| 6,893,459 B1 | 5/2005 | Macoviak |
| 6,893,460 B2 | 5/2005 | Spenser et al. |
| 6,908,481 B2 | 6/2005 | Cribier |
| 6,936,067 B2 | 8/2005 | Buchanan |
| 6,939,365 B1 | 9/2005 | Fogarty et al. |
| 6,964,682 B2 | 11/2005 | Nguyen-Thien-Nhon et al. |
| 6,974,476 B2 | 12/2005 | McGuckin, Jr. et al. |
| 6,978,176 B2 | 12/2005 | Lattouf |
| 7,011,681 B2 | 3/2006 | Vesely |
| 7,018,404 B2 | 3/2006 | Holmberg et al. |
| 7,018,406 B2 | 3/2006 | Seguin et al. |
| 7,018,408 B2 | 3/2006 | Bailey et al. |
| 7,025,760 B2 | 4/2006 | Gabbay |
| 7,037,334 B1 | 5/2006 | Hlavka et al. |
| 7,070,616 B2 | 7/2006 | Majercak et al. |
| 7,077,861 B2 | 7/2006 | Spence |
| 7,081,131 B2 | 7/2006 | Thornton |
| 7,097,659 B2 | 8/2006 | Woolfson et al. |
| 7,101,395 B2 | 9/2006 | Trenulis et al. |
| 7,101,396 B2 | 9/2006 | Artof et al. |
| 7,125,421 B2 | 10/2006 | Tremulis et al. |
| 7,147,663 B1 | 12/2006 | Berg et al. |
| 7,153,324 B2 | 12/2006 | Case et al. |
| 7,160,320 B2 | 1/2007 | Duran |
| 7,172,625 B2 | 2/2007 | Shu et al. |
| 7,186,265 B2 | 3/2007 | Sharkawy et al. |
| 7,195,641 B2 | 3/2007 | Palmaz et al. |
| 7,201,771 B2 | 4/2007 | Lane |
| 7,201,772 B2 | 4/2007 | Schwarmenthal et al. |
| 7,238,200 B2 | 7/2007 | Lee et al. |
| 7,252,682 B2 | 8/2007 | Seguin |
| 7,261,732 B2 | 8/2007 | Justino |
| 7,300,463 B2 | 11/2007 | Liddicoat |
| 7,311,730 B2 | 12/2007 | Gabbay |
| 7,377,941 B2 | 5/2008 | Rhee et al. |
| RE40,377 E | 6/2008 | Williamson, IV et al. |
| 7,422,603 B2 | 9/2008 | Lane |
| 7,429,269 B2 | 9/2008 | Schwarnmenthal et al. |
| 7,442,204 B2 | 10/2008 | Schwarnmenthal et al. |
| 7,445,630 B2 | 11/2008 | Lashinski et al. |
| 7,445,631 B2 | 11/2008 | Salahieh et al. |
| 7,468,073 B2 | 12/2008 | Johnson et al. |
| 7,470,285 B2 | 12/2008 | Nugent et al. |
| 7,510,575 B2 | 3/2009 | Spenser et al. |
| 7,513,909 B2 | 4/2009 | Lane et al. |
| 7,524,330 B2 | 4/2009 | Berreklouw |
| 7,534,261 B2 | 5/2009 | Friedman |
| 7,556,647 B2 | 7/2009 | Drews et al. |
| 7,569,072 B2 | 8/2009 | Berg et al. |
| 7,578,843 B2 | 8/2009 | Shu |
| 7,585,321 B2 | 9/2009 | Cribier |
| 7,591,848 B2 | 9/2009 | Alien |
| 7,597,711 B2 | 10/2009 | Drews et al. |
| 7,611,535 B2 | 11/2009 | Woolfson et al. |
| 7,618,446 B2 | 11/2009 | Andersen et al. |
| 7,618,447 B2 | 11/2009 | Case et al. |
| 7,622,276 B2 | 11/2009 | Cunanan et al. |
| 7,625,403 B2 | 12/2009 | Krivoruchko |
| 7,641,687 B2 | 1/2010 | Chinn et al. |
| 7,658,763 B2 | 2/2010 | Stobie |
| 7,682,390 B2 | 3/2010 | Seguin |
| 7,704,277 B2 | 4/2010 | Zakay et al. |
| 7,708,775 B2 | 5/2010 | Rowe et al. |
| 7,727,276 B2 | 6/2010 | Machiraju |
| 7,737,060 B2 | 6/2010 | Strickler et al. |
| 7,740,655 B2 | 6/2010 | Birdsall |
| 7,785,366 B2 | 8/2010 | Maurer et al. |
| 7,799,069 B2 | 9/2010 | Bailey et al. |
| 7,822,414 B2 | 10/2010 | Bender et al. |
| 7,862,610 B2 | 1/2011 | Quintessenza |
| 7,887,583 B2 | 2/2011 | Macoviak |
| 7,896,913 B2 | 3/2011 | Damm et al. |
| 7,947,072 B2 | 5/2011 | Yang et al. |
| 7,951,195 B2 | 5/2011 | Antonsson et al. |
| 7,951,197 B2 | 5/2011 | Lane et al. |
| 7,967,857 B2 | 6/2011 | Lane |
| 7,972,377 B2 | 7/2011 | Lane |
| 7,989,157 B2 | 8/2011 | Cunanan et al. |
| 8,062,355 B2 | 11/2011 | Figulla et al. |
| 8,167,932 B2 | 5/2012 | Bourang |
| 8,246,675 B2 | 8/2012 | Zegdi |
| 8,246,678 B2 | 8/2012 | Salahieh et al. |
| 8,308,798 B2 | 11/2012 | Pintor et al. |
| 8,323,335 B2 | 12/2012 | Rowe et al. |
| 8,348,998 B2 | 1/2013 | Pintor et al. |
| 8,353,953 B2 | 1/2013 | Giannetti et al. |
| 8,377,115 B2 | 2/2013 | Thompson |
| 8,398,708 B2 | 3/2013 | Meiri et al. |
| 8,449,605 B2 | 5/2013 | Lichtenstein et al. |
| 8,449,606 B2 | 5/2013 | Eliasen et al. |
| 8,460,173 B2 | 6/2013 | Schweich, Jr. et al. |
| 8,500,798 B2 | 8/2013 | Rowe et al. |
| 8,657,872 B2 | 2/2014 | Seguin |
| 8,663,322 B2 | 3/2014 | Keranen |
| 8,672,998 B2 | 3/2014 | Lichtenstein et al. |
| 8,734,507 B2 | 5/2014 | Keranen |
| 8,784,483 B2 | 7/2014 | Navia |
| 8,821,569 B2 | 9/2014 | Gurskis et al. |
| 9,078,747 B2 | 7/2015 | Conklin |
| 9,095,434 B2 | 8/2015 | Rowe |
| 9,119,718 B2 | 9/2015 | Keranen |
| 9,125,738 B2 | 9/2015 | Figulla et al. |

(56) References Cited

U.S. PATENT DOCUMENTS

| | | |
|---|---|---|
| 9,237,886 B2 | 1/2016 | Seguin et al. |
| 9,364,326 B2 | 6/2016 | Yaron |
| 9,463,268 B2 | 10/2016 | Spence |
| 9,474,599 B2 | 10/2016 | Keranen |
| 9,622,863 B2 | 4/2017 | Karapetian et al. |
| 2001/0021872 A1 | 9/2001 | Bailey et al. |
| 2001/0041914 A1 | 11/2001 | Frazier et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0040792 A1 | 2/2003 | Gabbay |
| 2003/0055495 A1 | 3/2003 | Pease et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulia et al. |
| 2003/0167089 A1 | 9/2003 | Lane |
| 2003/0225420 A1 | 12/2003 | Wardle |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0127982 A1 | 7/2004 | Machold et al. |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260390 A1 | 12/2004 | Sarac et al. |
| 2005/0010285 A1 | 1/2005 | Larnbrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0119735 A1 | 6/2005 | Spence et al. |
| 2005/0137682 A1 | 6/2005 | Justino |
| 2005/0137686 A1 | 6/2005 | Saiahieh et al. |
| 2005/0137687 A1 | 6/2005 | Saiahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Saiahieh et al. |
| 2005/0182483 A1 | 6/2005 | Osborne et al. |
| 2005/0151970 A1 | 7/2005 | DeGeorge et al. |
| 2005/0165477 A1 | 7/2005 | Anduiza et al. |
| 2005/0165479 A1 | 7/2005 | Drelvs et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0222674 A1 | 10/2005 | Paine |
| 2005/0234546 A1 | 10/2005 | Nugent et al. |
| 2005/0240259 A1 | 10/2005 | Sisken et al. |
| 2005/0240263 A1 | 10/2005 | Fogarty et al. |
| 2005/0251252 A1 | 11/2005 | Stobie |
| 2005/0283231 A1 | 12/2005 | Haug et al. |
| 2006/0025857 A1 | 2/2006 | Beroheirn et al. |
| 2006/0052867 A1 | 3/2006 | Revuelta et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0122634 A1 | 6/2006 | Ino et al. |
| 2006/0122692 A1 | 6/2006 | Gilad et al. |
| 2006/0149360 A1 | 7/2006 | Schwammenthal et al. |
| 2006/0161249 A1 | 7/2006 | Realyvasquez et al. |
| 2006/0195183 A1 | 8/2006 | Navia et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0229708 A1 | 10/2006 | Powell et al. |
| 2006/0235508 A1 | 10/2006 | Lane et al. |
| 2006/0241745 A1 | 10/2006 | Solem |
| 2006/0253191 A1 | 11/2006 | Salahieh et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162111 A1 | 7/2007 | Fukamachi et al. |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0239269 A1 | 10/2007 | Dolan et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2008/0021546 A1 | 1/2008 | Patz et al. |
| 2008/0033542 A1 | 2/2008 | Antonsson et al. |
| 2008/0033543 A1 | 2/2008 | Gurskis et al. |
| 2008/0082161 A1 | 4/2008 | Woo |
| 2008/0119875 A1 | 5/2008 | Ino et al. |
| 2008/0208330 A1 | 8/2008 | Keranen |
| 2008/0281411 A1 | 11/2008 | Berreklouw |
| 2009/0036903 A1 | 2/2009 | Ino et al. |
| 2009/0043381 A1 | 2/2009 | Macoviak et al. |
| 2009/0192602 A1 | 7/2009 | Kuehn |
| 2009/0192603 A1 | 7/2009 | Kuehn |
| 2009/0192604 A1 | 7/2009 | Gloss |
| 2009/0192605 A1 | 7/2009 | Gloss et al. |
| 2009/0192606 A1 | 7/2009 | Gloss et al. |
| 2009/0319037 A1 | 12/2009 | Rowe et al. |
| 2010/0145440 A1 | 6/2010 | Keranen |
| 2010/0161036 A1 | 6/2010 | Pintor et al. |
| 2010/0204785 A1 | 8/2010 | Alkhatib |
| 2010/0249894 A1 | 9/2010 | Oba et al. |
| 2010/0249908 A1 | 9/2010 | Chau et al. |
| 2010/0292784 A1 | 11/2010 | Giannetti et al. |
| 2010/0312333 A1 | 12/2010 | Navia et al. |
| 2010/0318184 A1 | 12/2010 | Spence |

(56) References Cited

U.S. PATENT DOCUMENTS

| | | |
|---|---|---|
| 2010/0331972 A1 | 12/2010 | Pintor et al. |
| 2011/0137410 A1 | 6/2011 | Hacohen |
| 2011/0147251 A1 | 6/2011 | Hodshon et al. |
| 2011/0190879 A1 | 8/2011 | Bobo et al. |
| 2011/0224785 A1 | 9/2011 | Hacohen |
| 2012/0059458 A1 | 3/2012 | Buchbinder et al. |
| 2012/0065729 A1 | 3/2012 | Pintor et al. |
| 2012/0087842 A1 | 4/2012 | Kristiansson et al. |
| 2012/0094406 A1 | 4/2012 | Patel et al. |
| 2012/0095116 A1 | 4/2012 | Kishi et al. |
| 2012/0150288 A1 | 6/2012 | Hodshon et al. |
| 2012/0165930 A1 | 6/2012 | Gifford, III et al. |
| 2012/0283820 A1 | 11/2012 | Tseng et al. |
| 2013/0175468 A1 | 7/2013 | Uehara |
| 2014/0074299 A1 | 3/2014 | Endou et al. |
| 2014/0172070 A1 | 6/2014 | Seguin |
| 2014/0379074 A1 | 12/2014 | Spence et al. |
| 2015/0173897 A1 | 6/2015 | Raanani et al. |
| 2015/0230921 A1 | 8/2015 | Chau et al. |
| 2015/0282931 A1 | 10/2015 | Brunnett et al. |
| 2015/0335428 A1 | 11/2015 | Keranen |
| 2015/0374493 A1 | 12/2015 | Yaron et al. |
| 2016/0074165 A1 | 3/2016 | Spence et al. |
| 2016/0095705 A1 | 4/2016 | Keranen et al. |
| 2016/0184095 A1 | 6/2016 | Spence et al. |
| 2016/0199177 A1 | 7/2016 | Spence et al. |
| 2016/0256276 A1 | 9/2016 | Yaron |
| 2017/0007399 A1 | 1/2017 | Keranen |
| 2017/0007402 A1 | 1/2017 | Zerkowski et al. |
| 2017/0217385 A1 | 8/2017 | Rinkleff et al. |

FOREIGN PATENT DOCUMENTS

| | | |
|---|---|---|
| DE | 19907646 A1 | 8/2000 |
| EP | 0125393 A1 | 11/1984 |
| EP | 0143246 A2 | 6/1985 |
| EP | 0592410 B1 | 10/1995 |
| EP | 0850607 A1 | 7/1998 |
| EP | 1432369 A1 | 6/2004 |
| EP | 1521550 A2 | 4/2005 |
| EP | 1296618 B1 | 1/2008 |
| EP | 1827314 B1 | 12/2010 |
| EP | 2620125 A1 | 7/2013 |
| EP | 2726018 A2 | 5/2014 |
| EP | 2806829 A2 | 12/2014 |
| WO | 9117720 A1 | 11/1991 |
| WO | 319213502 A1 | 8/1992 |
| WO | 9742871 A1 | 11/1997 |
| WO | 9806329 A1 | 2/1998 |
| WO | 9911201 A2 | 3/1999 |
| WO | 9551169 A1 | 10/1999 |
| WO | 9915112 A1 | 10/1999 |
| WO | 0032105 A1 | 6/2000 |
| WO | 0040176 A1 | 7/2000 |
| WO | 0060995 A2 | 10/2000 |
| WO | 0149213 A2 | 7/2001 |
| WO | 0154624 A1 | 8/2001 |
| WO | 0154625 A1 | 8/2001 |
| WO | 0247575 A2 | 6/2002 |
| WO | 02076347 | 10/2002 |
| WO | 2005084595 A1 | 9/2005 |
| WO | 2006011127 A2 | 2/2006 |
| WO | 2006086135 A2 | 8/2006 |
| WO | 2005102015 A3 | 4/2007 |
| WO | 2007067942 A1 | 6/2007 |
| WO | 2009155561 A2 | 12/2009 |
| WO | 2010121076 A2 | 10/2010 |
| WO | 2013110722 A2 | 8/2013 |
| WO | 2013114214 A2 | 8/2013 |
| WO | 2015023579 A1 | 2/2015 |
| WO | 2015023862 A2 | 2/2015 |
| WO | 2015127264 A1 | 8/2015 |
| WO | 2015198125 A1 | 12/2015 |
| WO | 2016038017 A1 | 3/2016 |
| WO | 2016040881 A1 | 3/2016 |
| WO | 2016130820 A1 | 8/2016 |

OTHER PUBLICATIONS

Sadowski, Jerzy; Kapelak, Boguslaw; Bartus, Krzysztof, "Sutureless Heart Valve Implantation—A Case Study," Touch Briefings, 2005, pp. 48-50.

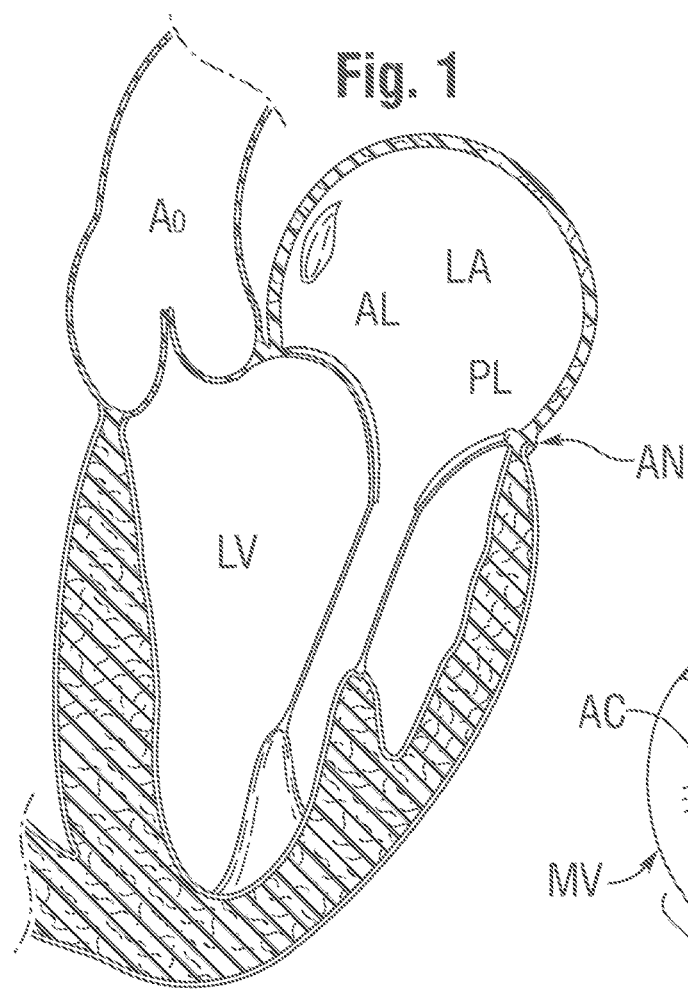
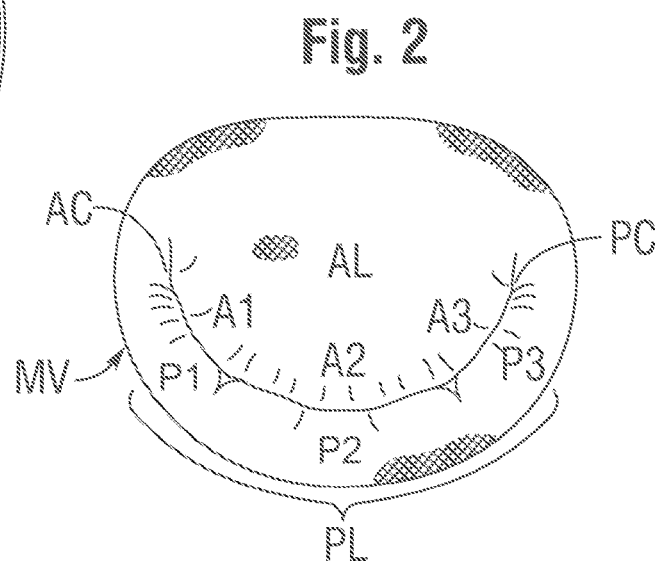
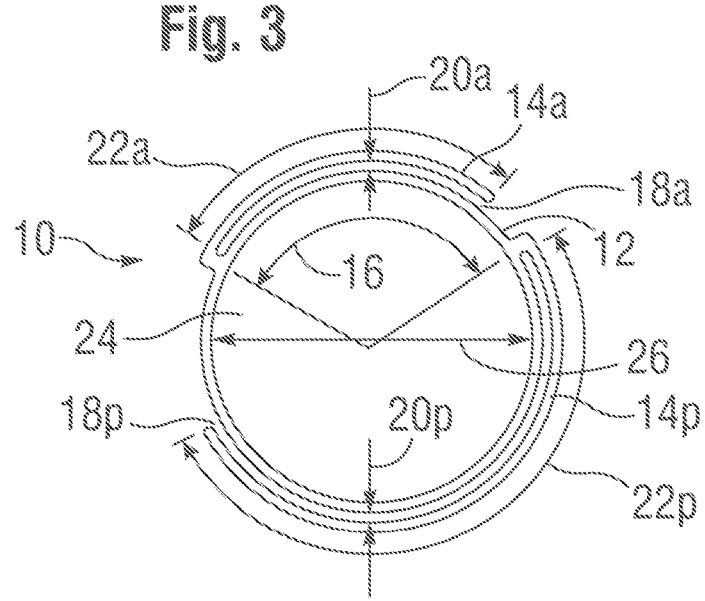

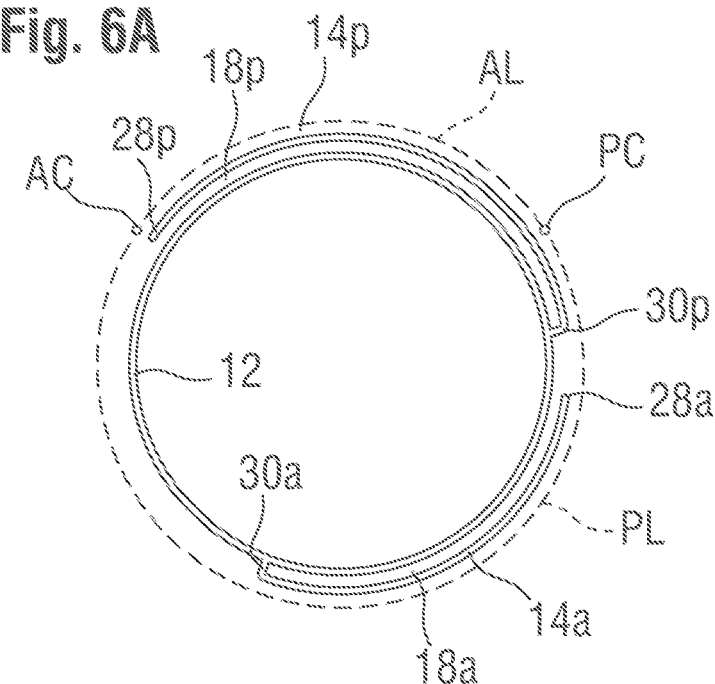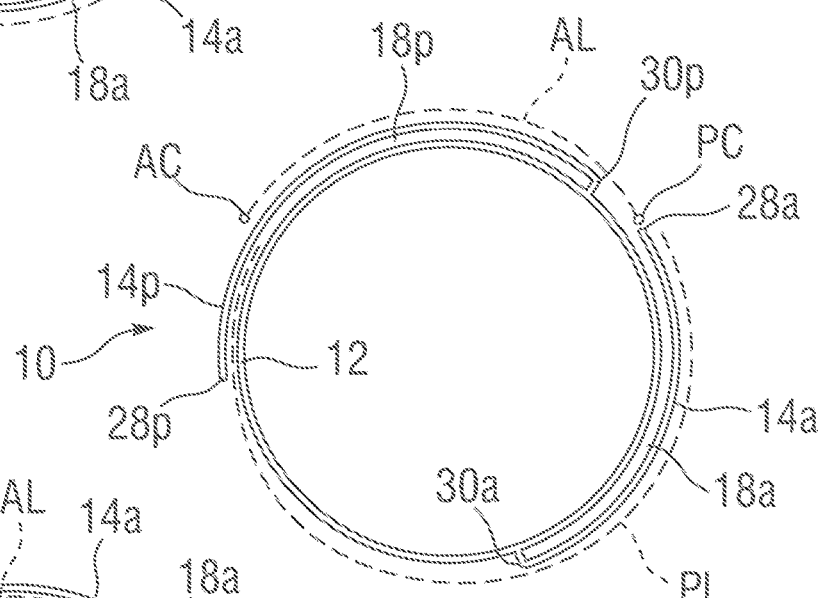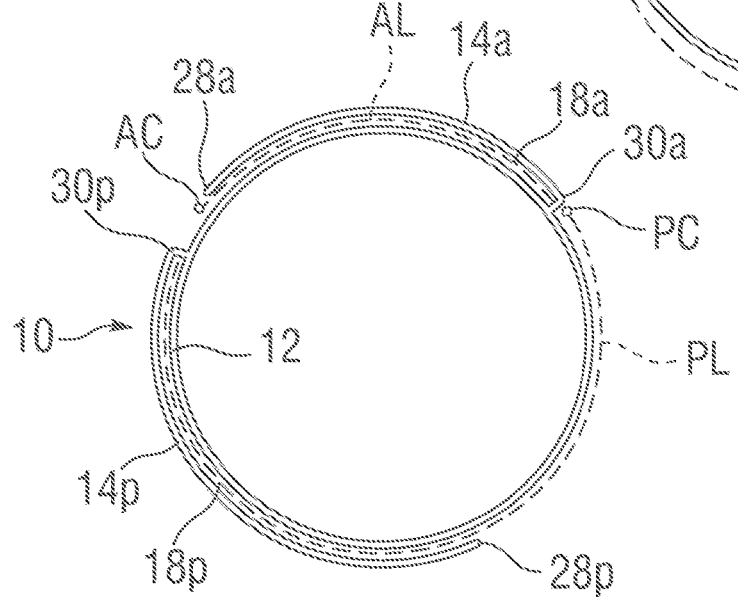

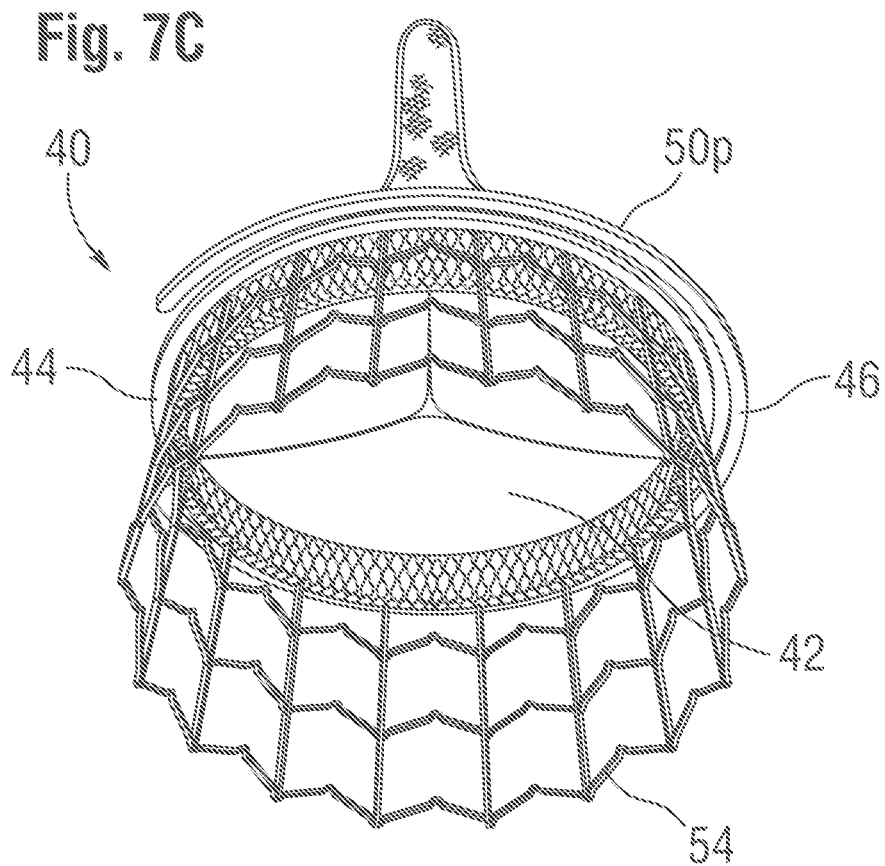
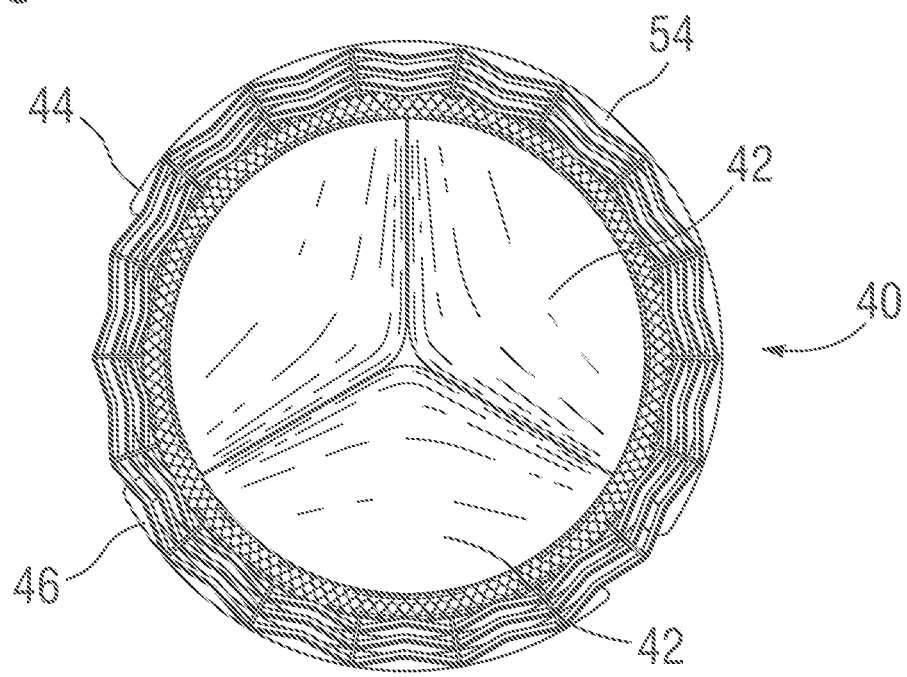

US 10,849,752 B2

METHODS FOR ANCHORING A DEVICE AT A NATIVE HEART VALVE ANNULUS

RELATED APPLICATIONS

The present application is a divisional of U.S. application Ser. No. 15/482,529, filed Apr. 7, 2017, which is a continuation of U.S. application Ser. No. 14/797,163, filed Jul. 12, 2015, which is a divisional of U.S. application Ser. No. 13/675,801, filed Nov. 13, 2012, now issued as U.S. Pat. No. 9,078,747, which claims priority to U.S. Provisional Application No. 61/578,758, filed Dec. 21, 2011, all of which are incorporated herein by reference in their entirety.

FIELD OF THE INVENTION

The current invention generally relates to heart valve repair and replacement devices and methods. More specifically, the current invention is directed to anchoring devices and methods for prosthetic heart valves and annuloplasty rings configured for rapid implantation and methods for implanting same.

BACKGROUND OF THE INVENTION

The heart is a hollow muscular organ of a somewhat conical form; it lies between the lungs in the middle mediastinum and is enclosed in the pericardium. The heart rests obliquely in the chest behind the body of the sternum and adjoining parts of the rib cartilages, and typically projects farther into the left than into the right half of the thoracic cavity so that about one-third is situated on the right and two-thirds on the left of the median plane. The heart is subdivided by septa into right and left halves, and a constriction subdivides each half of the organ into two cavities, the upper cavity being called the atrium, the lower the ventricle. The heart therefore consists of four chambers; the right and left atria, and right and left ventricles, with one-way flow valves between respective atria and ventricles and at the outlet from the ventricles.

The atrioventricular heart valves (i.e., the tricuspid and mitral valves) are located in the center of the heart between the atria and the ventricles of the heart, and play important roles in maintaining forward flow of blood. Atrioventricular valve dysfunction is also commonly known as "regurgitation" and affects well over one million people globally. The mitral and tricuspid valves are defined by fibrous rings of collagen, each called an annulus, which forms a part of the fibrous skeleton of the heart. The annulus provides peripheral attachments for the two cusps or leaflets of the mitral valve (called the anterior and posterior cusps) and the three cusps or leaflets of the tricuspid valve. The free edges of the leaflets connect to chordae tendinae from more than one papillary muscle. In a healthy heart, these muscles and their tendinous chords support the mitral and tricuspid valves, allowing the leaflets to resist the high pressure developed during contractions (pumping) of the left and right ventricles.

Although valve regurgitation often occurs due to the dilatation of the valve annulus, mitral and tricuspid valve function and competency frequently depend on the fine geometric and functional integrity of the valve's supporting structures, such as, for example, the associated subvalvular apparatus. The subvalvular apparatus of these heart valves include, among other things, the associated chordae tendinae and papillary muscles.

As seen in FIGS. 1 and 2, the mitral valve (MV) is a two-leaflet (or bicuspid) structure of connective tissue separating the left atrium (LA) from the left ventricle (LV). The mitral valve functions to maintain blood flow in one direction, i.e., from the left atrium toward the left ventricle during ventricular relaxation or diastole, while preventing back flow in the opposite direction during ventricular contraction or systole. The anterior leaflet (AL) and posterior leaflet (PL) are separated by the anterior commissure (AC) and posterior commissure (PC). The bases of the two valve leaflets are attached to a circular fibrous structure of the heart called the mitral annulus (AN), and the leaflet free edges are attached to chordae tendinae arising from the papillary muscles of the left ventricle. An anterior leaflet (AL) is relatively large and attaches to the anterior segment of the annulus, while a posterior leaflet (PL) is smaller but extends further circumferentially and attaches to the posterior segment of the annulus. The posterior leaflet presents three scallops identified as P1, P2, P3, while the corresponding non-scalloped parts of the anterior leaflet are identified as A1, A2, and A3, according to Carpentier's segmentation.

The tricuspid valve also has subvalvular structures, but is a tricuspid (i.e., three cusp or leaflet) structure as opposed to the bicuspid structure of the mitral valve. Some mitral and tricuspid valve replacement procedures involve the removal of these subvalvular structures. However, the subvalvular structures may play a role in maintaining the proper shape of the ventricles, and thus their preservation may be desirable, depending on the particular circumstances.

When the left ventricle contracts after filling with blood from the left atrium, the walls of the ventricle move inward and release some of the tension from the papillary muscle and chords. The blood pushed up against the under-surface of the mitral leaflets causes them to rise toward the annulus plane of the mitral valve. As they progress toward the annulus, the leading edges of the anterior and posterior leaflet come together forming a seal and closing the valve. In the healthy heart, leaflet coaptation occurs near the plane of the mitral annulus. The blood continues to be pressurized in the left ventricle until it is ejected into the aorta. Contraction of the papillary muscles is simultaneous with the contraction of the ventricle and serves to keep healthy valve leaflets tightly shut at peak contraction pressures exerted by the ventricle.

The native heart valves (such as the aortic, pulmonary, tricuspid, and mitral valves) serve critical functions in assuring the forward flow of an adequate supply of blood through the cardiovascular system. These heart valves can be rendered less effective by congenital, inflammatory, infectious conditions, or other disease. Such damage to the valves can result in serious cardiovascular compromise. Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood or regurgitation through the valve when the leaflets are supposed to coapt together to prevent regurgitation. Valve disease can be severely debilitating and even fatal if left untreated. For many years the definitive treatment for such disorders was the surgical repair or replacement of the valve during, for example, open heart surgery.

Various surgical techniques may be used to repair a diseased or damaged valve, which is typically used on minimally calcified valves. Surgical repair of the native valve is commonly conducted using so-called annuloplasty rings. Examples of annuloplasty rings, including methods of use for repairing native valves, are disclosed in U.S. Pat. No. 4,055,861, filed Apr. 9, 1976 and entitled "Support for a Natural Heart Valve"; U.S. Pat. No. 5,041,130, filed Nov. 30, 1989 and entitled "Flexible Annuloplasty Ring and Holder"; U.S. Pat. No. 6,558,416, filed Mar. 6, 2001 and entitled "Annuloplasty Ring Delivery Method"; and in co-pending U.S. patent application Ser. No. 13/019,506, filed Feb. 2, 2011 and entitled "Devices and Methods for Treating a Heart," the entire contents of each of which are incorporated herein by reference.

Sometimes actual replacement of the heart valve is the preferred option. Heart valve replacement may be indicated when there is a narrowing of a native heart valve, commonly referred to as stenosis, or when the native valve leaks or regurgitates, such as when the leaflets are calcified. Due to aortic stenosis and other heart valve diseases, thousands of patients undergo surgery each year wherein the defective native heart valve is replaced by a prosthetic valve, either bioprosthetic or mechanical. Prosthetic cardiac valves have been used for many years to treat cardiac valvular disorders.

When the valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective valves are deemed inoperable because their condition is too frail to withstand the procedure. By some estimates, about 30 to 50% of the subjects suffering from aortic stenosis who are older than 80 years cannot be operated on for aortic valve replacement.

Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For instance, U.S. Pat. No. 5,411,552 to Andersen et al. describes a collapsible valve percutaneously introduced in a compressed state through a catheter and expanded in the desired position by balloon inflation. Although these remote implantation techniques have shown great promise for treating certain patients, replacing a valve via surgical intervention is still the preferred treatment procedure. One hurdle to the acceptance of remote implantation is resistance from doctors who are understandably anxious about converting from an effective, if imperfect, regimen to a novel approach that promises great outcomes but is relatively foreign. In conjunction with the understandable caution exercised by surgeons in switching to new techniques of heart valve replacement, regulatory bodies around the world are moving slowly as well. Numerous successful clinical trials and follow-up studies are in process, but much more experience with these new technologies will be required before they are completely accepted.

In some situations, replacement of the native heart valve with a prosthetic heart valve may be the desired treatment. There are approximately 60,000 mitral valve replacements (MVR) each year and it is estimated that another 60,000 patients should receive a MVR due to increased risk of operation and age. The large majority of these replacements are accomplished through open-heart surgery, where a prosthetic heart valve is surgically implanted with the patient on pulmonary bypass. Such surgically implanted prosthetic valves have a long and proven record, with high success rates and clinical improvements noted after such valve replacement. However, it can be desirable to keep the time that the patient spends on pulmonary bypass to a minimum.

Surgeons relate that one of the most difficult tasks when attempting valve repair or replacement, either in open heart surgeries or minimally invasive heart valve implantations (e.g., through small incisions) is tying the suture knots that hold the valve or repair ring in position. A typical prosthetic mitral valve implant utilizes 12-24 sutures (commonly about 15) distributed evenly around and manually tied on one side of the sewing ring. The implantation process can be very time consuming and difficult to perform, particularly through minimal size incisions due to the numerous pairs of sutures that need to be precisely placed in the annulus and the knots that are typically used to secure the sutures when the valve is parachuted into place. Similarly, in a valve repair procedure numerous pairs of sutures must be precisely placed around the native annulus to attach the repair device. Minimizing or even eliminating the need to use suture (and/or to tie suture knots) for attachment of prosthetic valves or repair devices would greatly decrease the time of the procedure and/or facilitate the use of smaller incisions, thus reducing infection risk, reducing the need for blood transfusions, reducing the time spent on bypass, and allowing more rapid recovery.

Accordingly, there is a need for an improved device and associated method of use wherein a prosthetic valve or valve repair device can be implanted in a more efficient procedure that reduces the time required on extracorporeal circulation and/or catheterization. It is desirable that such a device and method be capable of helping patients with defective valves that are deemed inoperable because their condition is too frail to withstand a lengthy conventional surgical procedure. The present invention addresses these needs and others.

SUMMARY OF THE INVENTION

A valve repair or replacement device for implantation at a native valve annulus and method of implanting the same is disclosed. The device may be a prosthetic valve, annuloplasty ring, or other device for implantation at the native valve annulus. The device has a central portion with one or more anchors extending therefrom from fixed ends secured to the central portion, with the anchors terminating at free ends. The anchors run substantially parallel to the circumference of the central portion in a curved fashion, forming leaflet-receiving slots between the anchors and central portion. The device is configured to be positioned at the native valve annulus, and then rotated (twisted) to place the anchors underneath the resident valve leaflets, with the resident valve leaflets sliding into the leaflet-receiving slots until the device is fully seated. The leaflets are then held within the slots, which may include inward pressure from the anchor arms that press the leaflets between the anchor arms and the central portion of the device.

The anchors may extend from the central portion, and may include a cross-section configured to have a different stiffness in-plane than the stiffness out-of-plane. There may be one, two, three, four, or more anchors extending from the central portion. The anchors may extend from the central portion at different positions around the circumference thereof, and may be generally equidistantly positioned around the circumference. The anchors may be formed of metal or polymer or other suitable material, and the device may include a cloth covering. The device may include radiopaque markers and other structures to enhance visibility during implantation. For example, an anchor member may have one or more radiopaque markers positioned thereon, such as at the tip of the free end and/or at the fixed end.

The assembly may form a prosthetic valve formed by support frame and valve leaflets, with the support frame having a central portion and one or more curved anchors extending therefrom to form at least one slot between the anchor(s) and central portion, with the at least one slot sized to slidingly receive a proximal portion of a heart valve leaflet therein. The anchors and slots may be preferably sized and configured to engage resident leaflets. For example, at least one slot may have a width of similar size to the thickness of a native valve leaflet.

A device for treating a heart according to an embodiment of the invention comprises a prosthetic valve having a support frame and a valve portion. The valve portion may include a plurality of leaflets secured to the support frame and configured to coapt to permit blood flow in a first direction through the valve portion and to prevent blood flow in a second direction through the valve portion, wherein the first direction is opposite to the second direction, wherein the support frame comprises one or more attachment structures configured to be attached, and/or to otherwise facilitate attachment of the device, to tissue at or adjacent an annulus of a native heart valve.

The prosthetic valve may be configured for surgical implantation, either via traditional open-heart or minimally invasive techniques, and/or via catheterization. The support frame may have supplemental attachment structures (i.e., in addition to the anchors) for securing the prosthetic valve at a desired location at a native heart valve annulus. For example, the support frame may comprise a sewing ring configured to be sutured to tissue of the annulus of the native heart valve, and/or may include other attachment structures configured to secure the support frame at the valve annulus using no (or minimal) suture, such as an expandable stent structure, clamps, skirts, or other elements configured to engage tissue of, or adjacent to, the native annulus in order to secure the prosthetic valve at the desired position. Examples of sutureless securement devices and methods for use with the current invention are disclosed in U.S. patent application Ser. No. 12/821,628, filed Jun. 23, 2010 and entitled "Unitary Quick-Connect Prosthetic Heart Valve and Deployment System and Methods," and also in U.S. patent application Ser. No. 13/167,639, filed Jun. 23, 2011 and entitled "Systems and Methods for Rapidly Deploying Surgical Heart Valves," the entire contents of each of which are expressly incorporated herein by reference.

An embodiment of the invention is a prosthetic heart valve assembly for replacing a resident heart valve, comprising a prosthetic valve and anchors extending therefrom. The prosthetic valve may have a support frame and a valve portion. The valve portion is a one-way valve, which may have a plurality of leaflets secured to the support frame about a central axis of the prosthetic valve to an internal flow lumen and configured to coapt to permit blood flow in a first direction through the internal flow lumen and to prevent blood flow in a second direction through the internal flow lumen. The prosthetic valve has an exterior surface, which may be configured to engage tissue of a heart. At least one anchor member extends from the support frame, the anchor member comprising a proximal fixed end secured to the support frame and a distal free end. The anchor member extends at least partially around the circumference of the prosthetic valve (radially about the central axis thereof) and substantially parallel to the prosthetic valve exterior to define a leaflet-receiving slot configured to slidingly receive a leaflet of a heart valve. The leaflet-receiving slot extends in continuous, unbroken fashion from the proximal fixed end of the anchor member to the distal free end of the anchor member. The slot is sized and configured to slidingly receive and hold a desired valve leaflet of a resident valve, where a resident valve is a native heart valve or a previously-implanted prosthetic valve. Depending on the particular application, the slot may have a length of 0.25 to 3.5 inches and a width of 0.005 to 0.25 inches.

The prosthetic valve may be substantially tubular, with the exterior surface forming a substantially continuously curved surface about the circumference thereof, with the anchor member forming a curve which parallels the curved surface of the exterior surface of the valve.

A valve assembly according to the invention may form a prosthetic mitral valve assembly with first and second anchor members defining first and second leaflet-receiving slots and having first and second fixed ends and first and second free ends, respectively. Each slot extends in continuous, unbroken fashion from the anchor fixed end to the anchor free end. The anchors can be sized and positioned to engage the anterior and posterior leaflets of a native mitral valve, so that the slots are sized to receive these leaflets. The first and second anchors may have fixed ends which are spaced at least 90 degrees apart, and more specifically about 100 to 140 degrees apart, and more specifically 120 degrees apart, about the circumference of the device, with the anchor extending in the same rotational direction (e.g., clockwise) about the circumference of the device. The first anchor member may pass around the circumference of the prosthetic valve through an angle of at least 90 degrees, with the second anchor passing around the circumference of the prosthetic valve through an angle of at least 120 degrees.

An assembly according to the invention may form an annuloplasty ring having a support ring having a circumference and comprising a central opening defining a flow axis through which fluid may flow, a covering around the support ring, the covering comprising an outer surface, and a first anchor member extending from the support frame. The first anchor may have a first proximal fixed end secured to the support ring and a first distal free end, wherein the first anchor member extends around at least partially around a circumference of the support ring and substantially parallel to outer surface of the covering to define a first leaflet-receiving slot configured to receive a leaflet of a heart valve. The first leaflet-receiving slot may preferably extend in continuous, unbroken fashion from the first proximal fixed end to the first distal free end. The first anchor member may extend around the circumference of the prosthetic valve through an angle of at least 90 degrees.

An annuloplasty ring may further include additional anchor members. For example, it may include a second anchor member having a second proximal fixed end secured to the support ring and a second distal free end, wherein the second anchor member extends at least partially around the circumference of the annuloplasty ring and substantially parallel to the exterior thereof to define a second leaflet-receiving slot configured to receive a second leaflet of a heart valve. The second leaflet-receiving slot may extend in continuous, unbroken fashion from the second proximal fixed end to the second distal free end. The second proximal fixed end may be circumferentially displaced from the first anchor proximal fixed end by an angle of at least 90 degrees, by an angle of between 100 and 140 degrees, or by an angle of about 120 degrees. The first anchor may extends around the circumference of the annuloplasty ring through an angle of between 90 and 120 degrees, and the second anchor may extend around the circumference of the annuloplasty ring through an angle of between 150 and 240 degrees. The support ring may be substantially circular, substantially D-shaped, and/or substantially saddle-shaped.

Methods of implanting a device (e.g., annuloplasty ring, prosthetic valve, etc.) at a native valve annulus can include providing a device comprising a central portion, a first curved anchor extending from a first fixed end secured to the central portion and passing generally parallel to an outer surface thereof to a first free end of the first curved anchor to form a first leaflet-receiving slot, a second curved anchor extending from a second fixed end secured to the central portion and passing generally parallel to an outer surface thereof to a second free end to form a second leaflet-receiving slot, wherein the central portion defines a flow orifice with a flow axis therethrough. The method may include positioning the device with the first curved anchor and second curved anchor adjacent the native valve annulus, with the fluid flow axis of the device generally parallel to a fluid flow path through the native valve annulus, and with the first free end positioned adjacent a first commissure of a resident valve at the native valve annulus; placing the first free end underneath a first resident valve leaflet; rotating the device substantially about the fluid flow axis thereof to advance the first free end underneath the first resident valve leaflet and thereby slidingly advancing the first resident valve leaflet into the first leaflet-receiving slot; monitoring the position of the second free end with respect to a second commissure of the resident valve; and stopping rotation of the device about the fluid flow axis once the second free end is adjacent the second commissure of the resident valve. Once the second free end is adjacent the second commissure, the surgeon or other user can place the second free end underneath a second resident valve leaflet; recommencing rotating the device substantially about the fluid flow axis thereof to advance the second free end underneath the second resident valve leaflet and thereby slidingly advancing the second resident valve leaflet into the second leaflet-receiving slot while also further advancing the first free end underneath the first resident valve leaflet and further slidingly advancing the first resident valve leaflet into the first leaflet-receiving slot; and stop rotation of the device when the first resident valve leaflet is slidingly advanced into the first leaflet-receiving slot at a position adjacent the first fixed end, whereby deployment of the device is completed.

The native valve annulus may be a mitral valve annulus or a tricuspid valve annulus. If the native annulus is a tricuspid annulus, the device may include three anchors spaced around the perimeter of the device, with each anchor configured to slidingly receive one of the three valve leaflets of the resident tricuspid valve. Where the native valve annulus is a mitral valve annulus with intact native mitral valve leaflets, the first commissure may be a PC commissure of a native mitral valve, the first leaflet may be an anterior leaflet of the native mitral valve, the second commissure may be an AC commissure of the native mitral valve, and the second leaflet may be a posterior leaflet of the native mitral valve.

Methods of implanting the device include open heart surgery, including surgery where prior to positioning the device adjacent the native valve annulus, the surgeon or other user temporarily ceases heart function of the heart and places the patient on cardiopulmonary bypass. After completing deployment of the device, the heart function of the heart may be resumed and the patient then removed from cardiopulmonary bypass.

Methods of the invention include providing a valve repair or replacement device. The device may comprise an annuloplasty ring with one or more anchors extending therefrom, or may comprise a prosthetic valve with a support frame and leaflets with the leaflets secured to the support frame to form a one-way valve structure and with one or more anchors extending from the support frame. Each anchor has a proximal end secured to the support frame and a free distal end, with a slot defined between the support frame and the anchor. The anchor is positioned adjacent a commissure point of the native valve, and the free end is positioned underneath a native leaflet of the valve (and below the native heart valve annulus). The device (e.g., annuloplasty ring or prosthetic heart valve) is rotated about its central axis to advance the anchor underneath the native leaflet, so that the native leaflet is slidingly advanced into the slot. Advancement and securement can be performed in an open-heart or minimally-invasive procedure. The central portion (e.g., ring portion or support frame) may comprise a sewing ring, and securing the support frame to the tissue of the native heart valve annulus may include suturing the sewing ring to tissue of the native heart valve annulus. The device may comprise a stent, with the stent being expanded into contact with native tissue before, during, or after the anchor(s) are rotated underneath the resident leaflets). The native valve annulus may be of any heart valve, with particular application to mitral and tricuspid valves.

After the central portion is secured to the native valve annulus, the surgeon or other user may add one or more stitches or other securing device/methods to secure the device to the local tissue in order to prevent the device from rotating back out of its deployed position. In such a deployment, the anchors hold the device to prevent movement up, down, sideways, etc., while the sutures or other tissue connectors serve to prevent the device from rotating such that the leaflets rotatingly slide out of the slots to be released from the anchors.

The method may include temporarily ceasing heart function of the heart and placing the patient on cardiopulmonary bypass, performing various steps (such as advancement and securing of the prosthetic valve to the native annulus), and then resuming heart function of the heart and removing the patient from cardiopulmonary bypass. Deployment of the device may occur with the patient on bypass, or may occur with the patient's heart beating (e.g., after the patient is removed from bypass, with heart function restarted) and with the surgeon or other user monitoring the heart function and/or ventricular shape as the length adjustments are made.

Methods of the invention may include, prior to securing the support frame to the tissue of the native heart valve annulus, removing some native valve leaflets and/or subvalvular structure (e.g., chordae tendinae) from the heart.

The foregoing and other objects, features, and advantages of the invention will become more apparent from the following detailed description, which proceeds with reference to the accompanying figures.

BRIEF DESCRIPTION OF THE DRAWINGS

FIG. 1 is a cross-sectional view of the left side of the human heart showing the left atrium separated from the left ventricle by the mitral valve;

FIG. 2 is a surgeon's or plan view of a mitral valve in the closed position illustrating the anterior leaflet (AL) and the posterior leaflet (PL) attached to the annulus (AN), and indicating identifiable leaflet segments;

FIG. 3 is a bottom view of an embodiment of a device according to an embodiment of the invention;

FIGS. 6A-6C are top views of a device being deployed in a mitral valve annulus according to the invention;

FIGS. 7A-7D are side, bottom, perspective, and top views, respectively of a prosthetic heart valve according to an embodiment of the invention;

DESCRIPTION OF THE PREFERRED EMBODIMENTS

Figure 4:
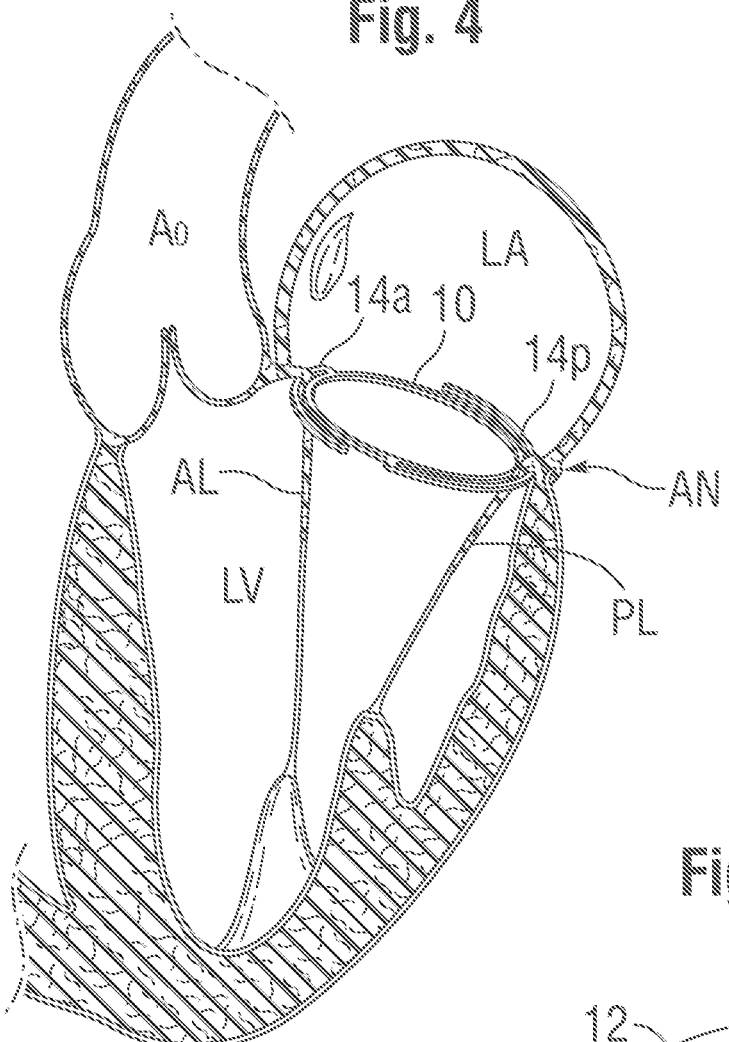
FIGS. 4 and 5 are perspective (in partial cross-section) and top views of an embodiment of a device deployed in a heart according to an embodiment of the invention.

The invention is an anchoring device, including prosthetic heart valves and annuloplasty rings and other devices using that anchoring device, for securement within a patient, such as in a native heart valve annulus in a human heart. The device has particular applicability to devices to be secured at the annulus of a valve (such as the mitral and tricuspid valves) which has subvalvular structures such as chordae tendinae. A mitral valve and its subvalvular structure are depicted in FIGS. 1 and 2.

FIG. 3 depicts a device 10 for anchoring a prosthetic heart valve or repair ring to the mitral annulus of a heart. The device 10 may be made of a metal such as stainless steel, although other materials (metal or non-metal) may be suitable. The device 10 is composed of a central ring 12 having two semi-circular anchors, namely an anterior anchor 14a and a posterior anchor 14p, attached to and extending from the central ring 12 at positions spaced apart around the circumference of the ring by an angle 16 of approximately 120 degrees. This angle and spacing divides the device 10 into approximately ⅓ and ⅔ sections, thus approximating the proportions of the anterior leaflet and posterior leaflet of a native mitral valve. The anchors 14a, 14p are spaced slightly away from and run substantially parallel to the outer circumference of the central ring 12, and define an anterior leaflet receiving slot 18a and posterior leaflet receiving slot 18p, respectively. The leaflet receiving slots 18a, 18p have a width 20a, 20p which is generally on the order of the thickness of the anterior and posterior leaflets of a mitral valve, i.e., the slots 18a, 18p have a width of about 0.005 to 0.25 inches. These slot widths 20a, 20p are sufficient to permit the anterior and posterior leaflets of a mitral valve to slidingly enter the slots 18a, 18p. The slots 18a, 18p have lengths 22a, 22p sufficient to receive a substantial portion of the respective mitral valve leaflets. The length 22a of the anterior leaflet receiving slot 18a may be between about 0.25 to 3.5 inches, while the length 22p of the posterior leaflet receiving slot 18p may be between about 0.25 and 3.5 inches. The central ring 12 defines an inner opening 24 having an inner diameter 26. If the device 10 is part of a prosthetic heart valve (e.g., part of a support stent of a prosthetic heart valve), the inner diameter 20 may be between 0.75 to 1.5 inches. If the device 10 is part of a valve repair device such as an annuloplasty ring, the inner diameter may be between 0.75 to 1.5 inches.

Figure 5:
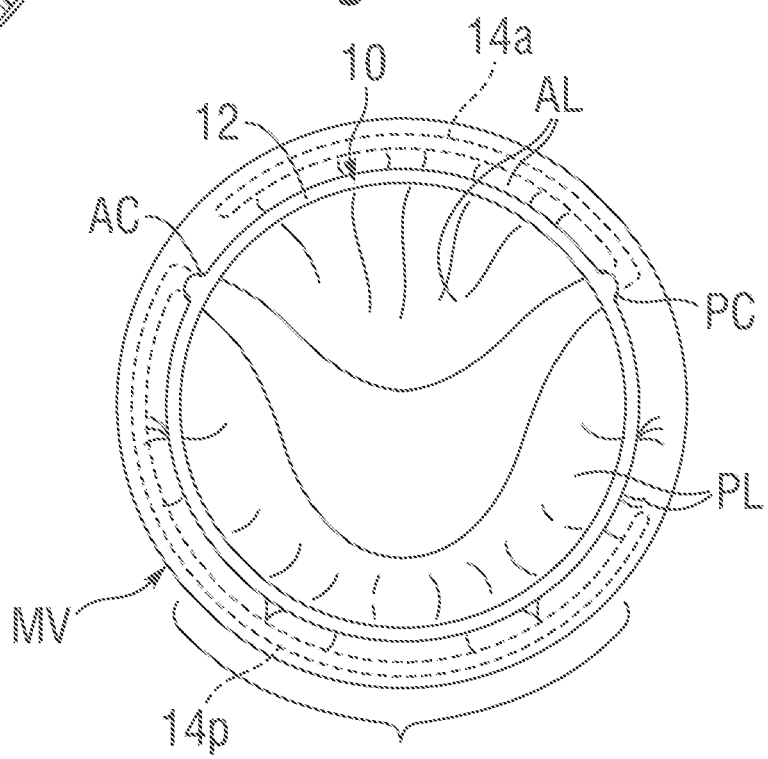
Figure 7A:
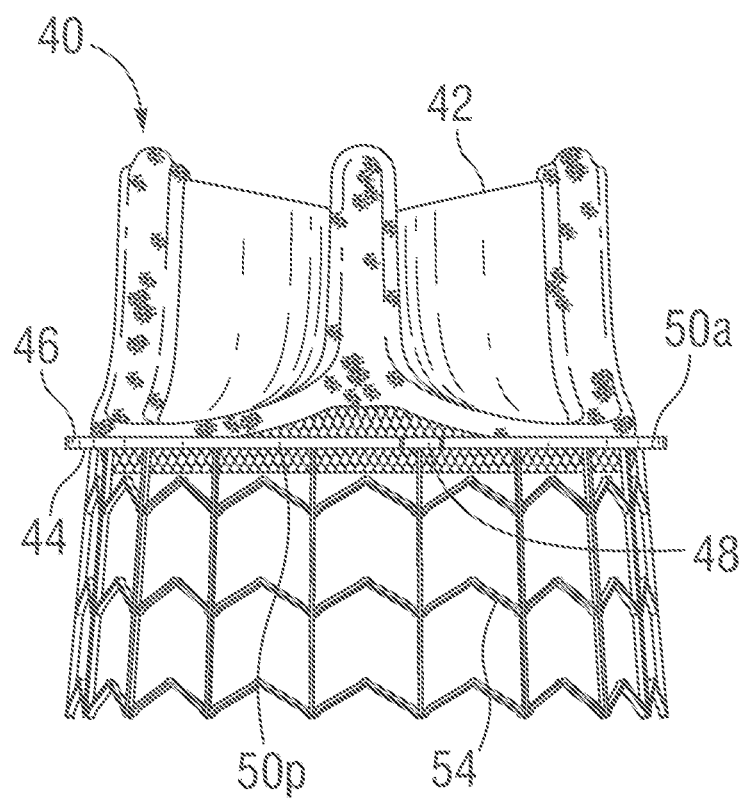
Figure 7B:
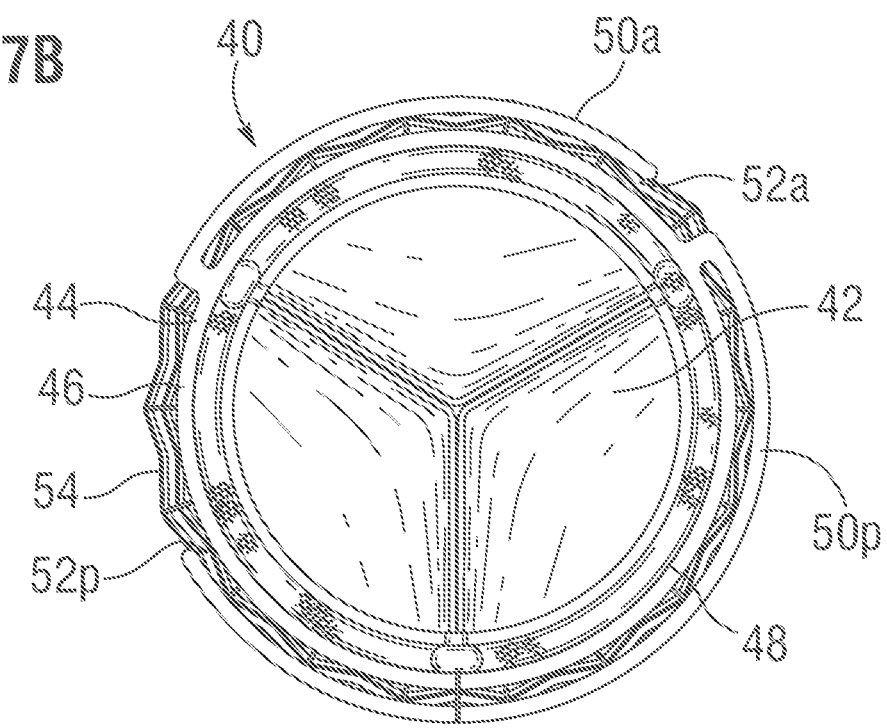

FIGS. 4 and 5 depict the device 10 anchored in a mitral valve annulus AN. The anterior leaflet AL is positioned within the anterior leaflet slot 18a such that the slot 18a holds a proximal portion of the anterior leaflet AL (with the proximal portion of the leaflet being adjacent the annulus AN, as opposed to a distal portion which is adjacent the leaflet edge). Similarly, the posterior leaflet PL is positioned within the posterior leaflet slot 18p such that the slot 18p receives a proximal portion of the posterior leaflet PL (with the proximal portion of the leaflet being adjacent the annulus AN, as opposed to a distal portion which is adjacent the leaflet edge). The anterior and posterior anchors 14a,14p are thus positioned between their respective leaflets AL, PL and the ventricle wall, while the central ring 12 is positioned within the mitral valve annulus AN. The anchors 14a, 14p and slots 18a, 18p thus prevent migration of the device, e.g., into the atrium during systole or into the ventricle during diastole. The leaflet slots 18a, 18p serve to grip the leaflets AL, PL to anchor the device 10 in the desired position in the annulus AN.

FIGS. 6A-6C depict schematically the installation of the device 10, as viewed from the left atrium (i.e., looking through the mitral valve into the left ventricle). In FIG. 6A, the device 10 is positioned with the central ring 12 generally centrally positioned in the mitral valve annulus AN, and with the posterior anchor free end 28p adjacent the AC commissure. The posterior anchor free end 28p is inserted (e.g., by manipulating the device 10 as a whole and/or by bending the posterior anchor free end 28p away/downward from its normal position adjacent the central ring 12) between the anterior and posterior leaflets so it is positioned underneath the posterior leaflet PL, and the device 10 is then rotated counter-clockwise, with the posterior leaflet PL sliding into the posterior anchor slot 18p, to the point where the anterior anchor free end 28a is adjacent the PC commissure, as depicted in FIG. 6B. The anterior anchor free end 28a is then inserted (e.g., by manipulating the device 10 as a whole and/or by bending the anterior anchor free end 28a away/downward from its normal position adjacent the central ring 12) between the anterior and posterior leaflets so it is positioned underneath the anterior leaflet AL, and the device 10 is further rotated clockwise with the anterior leaflet AL sliding into the anterior anchor slot 18a (and the posterior leaflet PL further sliding into the posterior anchor slot 18b) until the device is fully seated. When fully seated, as depicted in FIG. 6C, both anchors 14a, 14p are beneath their respective leaflets AL, PL, the attachment bar 30a of the anterior leaflet anchor 14a is positioned at the PC commissure, and the attachment bar 30p of the posterior leaflet anchor 14p is positioned at the AC commissure.

Figure 8A:
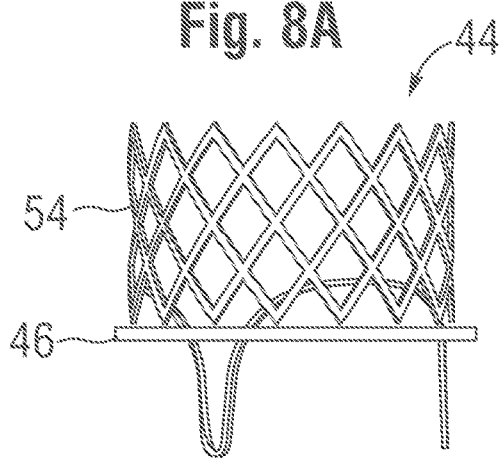
FIGS. 8A and 8B are side views of a device according to an embodiment of the invention.
Figure 8B:
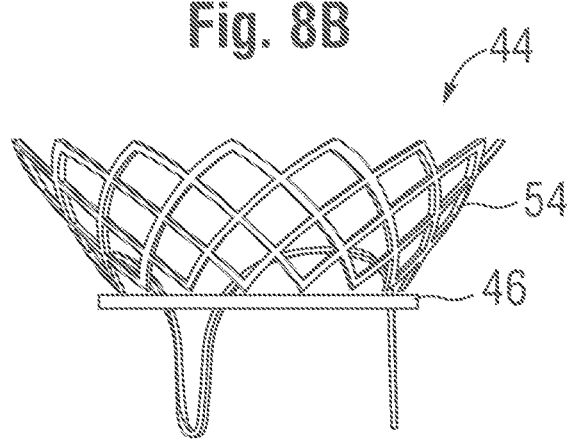

FIGS. 7A-7D depict a prosthetic mitral valve assembly 40 utilizing an anchoring assembly of the invention. The valve assembly 40 has a tri-leaflet valve portion 42 secured to a support structure 44. The support structure 44 includes an anchoring device 46, which itself has a central ring 48 with posterior and anterior anchors 50a, 50p defining posterior and anterior slots 52a, 52p configured to slidingly receive posterior and anterior leaflets of a mitral valve. The assembly 40 further includes an upstream stent structure 54 which is configured to be expanded into engagement with surrounding tissue, such as with the atrium wall. The stent could be either self-expanding or balloon expandable. The stent 54 would preferably be crimped (in the case of balloon expandable) or restrained (in the case of self-expandable), to a relatively small delivery diameter, as depicted in FIG. 8A, for delivery. Once the anchor portion was fully engaged with the native valve leaflets (i.e., rotated into engagement), the stent could be deployed to its expanded condition, as depicted in FIG. 8B. If the stent portion 54 were self-expanding, the delivery catheter would need a sheath to restrain the stent in its compressed delivery configuration. If the stent were balloon expandable, the delivery catheter would need a balloon or similar radially expansion device to radially expand the stent.

Figure 9A:
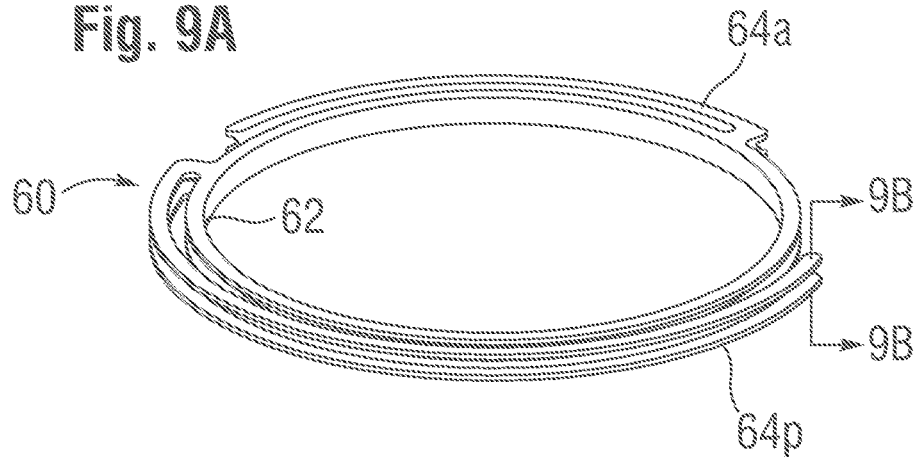
FIGS. 9A and 9B are perspective and close-up cross-sectional views of a device according to an embodiment of the invention.
Figure 9B:
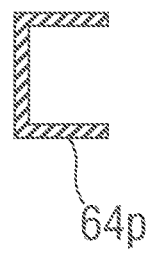

The configurations of various elements could vary at different positions on the assembly. For example, the cross-sectional shape of the anchors and/or central ring could be other than rectangular, and/or could vary along their lengths. For example, as depicted in FIGS. 9A and 9B, an anchor assembly 60 could have a central ring 62, with anchor portions 64a, 64p having a "C"-shaped channel cross section. The cross section shape could be designed such that the in-plane stiffness of the anchors was substantially less than their out-of-plane stiffness, or vice-versa. Such differential stiffness could help the anchors conform to the native annulus during insertion while still providing high retention forces in the axial direction.

Figure 10:
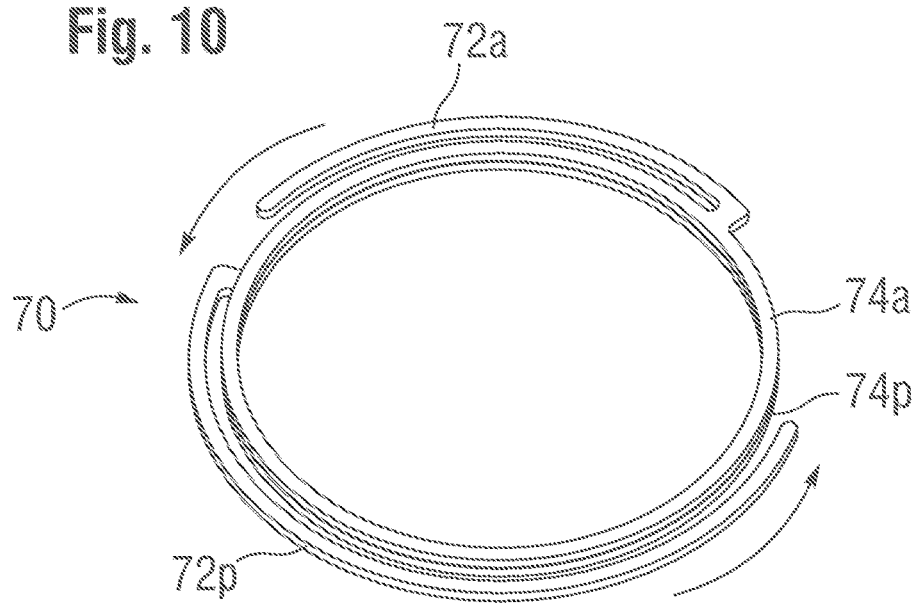
FIG. 10 is a perspective view of a device according to an embodiment of the invention.

FIG. 10 depicts a further embodiment of the device, wherein an anchor assembly 70 has a posterior anchor 72p and an anterior anchor 72a, but the anchors 72a, 72p are secured to separate assembly ring portions 74a, 74p. These separate ring portions 74a, 74p can rotate with respect to each other, thereby permitting separate (independent) rotation of the anchors 72a, 72p with respect to each other. Such independent rotation of the anchors 72a, 72p could make installation of the device easier for the surgeon or other user.

Figure 11:
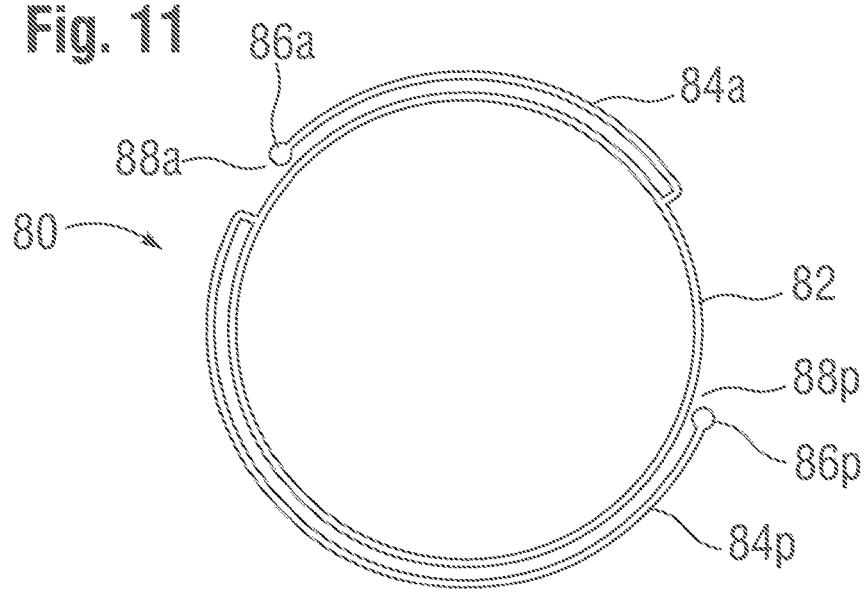
FIG. 11 is a top view of a device according to an embodiment of the invention.

Various modifications could be made to promote ease of use. For example, an anchor device 80 portion could have a central ring 82 and anchors 84a, 84p having rounded or otherwise blunted ends, such as the spherical-tipped ends 86a, 86p depicted in FIG. 11, to reduce the potential for the tips to snag on or traumatize the tissue of the leaflets, ventricle wall, chordae, etc., as the leaflets are slid into the slots 88a, 88p. Such structures could make it easier for the anchors 84a, 84p to be threaded behind the valve leaflets. The rounded structures could be formed as a unitary portion (i.e., at the same time, of the same material, etc.) with the anchors, or could be separate pieces attached to the anchors during manufacture. For example, the rounded portions could be formed from PTFE which is press-fit and/or glued to the anchors.

An anchoring device according to the invention could use various materials, and could include coverings, etc. For example, the structure of the anchoring device (formed of, e.g., metal) could include a cloth covering. Such coverings could serve multiple purposes. For example, covering the device with a biocompatible covering which encourages tissue ingrowth, such as PTFE cloth, would encourage the patient's native tissue to attach to the device over time, possibly reducing tissue irritation and potential damage from metal-on-tissue contact. The tissue ingrowth could also assist to improve the anchoring of the device, by providing mechanical stability and thereby reduce the chance of migration and embolization. The covering, especially a cloth covering, could also provide the ability for a surgeon or other user to use sutures to further secure the device in place. A flexible/resilient covering, such as cloth, could also provide a surface which would "give way" (e.g., be compressed) to permit the leaflets to be slid into the slots, but would also push back (i.e., rebound) into the slots to engage the leaflets once in place and assist in holding the device in place. A covering could also be used to hold a lubricious coating, such as glycerol, which could facilitate the threading of the anchors between the leaflets and the ventricle.

Coverings, if present, could be configured to bioresorb or otherwise degrade over time, or could be formed from material(s) that will not biodegrade/bioresorb over time. Examples of such materials for potential use with the invention include PTFEs, polyesters, nylons, and others.

The structural support portions of devices according to the invention could be formed from metals or non-metals, including stainless steel, nitinol, titanium, CoCr, alloys, polymeric materials, and other biocompatible materials. The structural support portions (i.e., the central ring and anchors) may preferably be formed from materials which are substantially rigid with minimal elasticity, and which are not easily plastically deformed. Devices according to the invention may include radiopaque markers and other structures to enhance visibility during implantation. For example, an anchor member may have one or more radiopaque markers positioned thereon, such as at the tip of the free end and/or at the fixed end. Such radiopaque markers may be formed from highly-radiopaque materials (e.g., gold, platinum) mounted on, embedded in, formed with, or otherwise secured to the structural support and/or other portions of the device.

Figure 12:
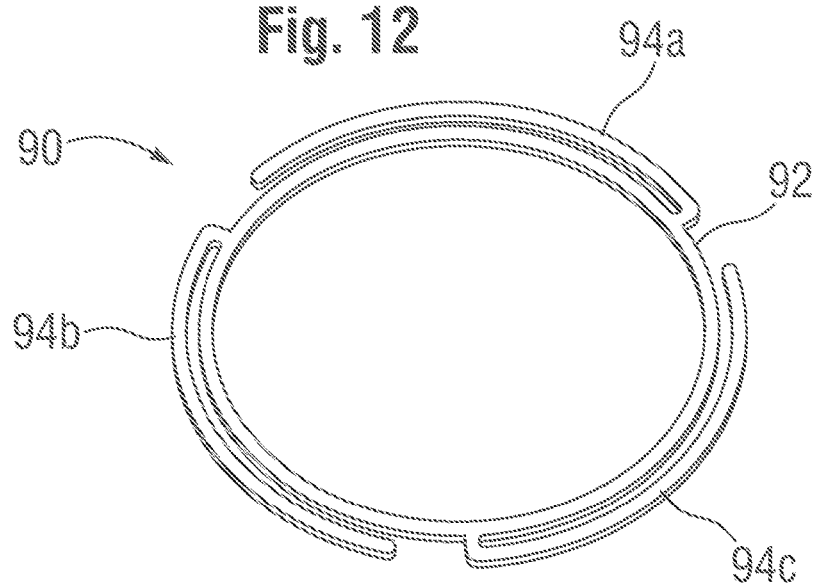
FIG. 12 is a top view of a device according to an embodiment of the invention.

FIG. 12 depicts a further embodiment of an anchor assembly 90, where a central ring 92 has three anchors 94a, 94b, 94c positioned around the perimeter of the device. In the specific embodiment depicted, the anchors 94a, 94b, 94c are spaced at about 120 degrees to each other, although other spacings are within the scope of the invention. The three-anchor design could be applicable for deployment at non-mitral valve locations, such as at the tricuspid valve position (i.e., the valve and annulus between the right ventricle and right atrium). Alternatively, such an assembly could be used for anchoring at the mitral valve, where one of the arms (e.g., arm 94a) was used to be secured to the anterior leaflet, and the other two arms (e.g., arms 94a, 94c) were used to be secured to the posterior leaflet. In order to properly thread the device into place, the surgeon or other user might need to form an incision in the posterior leaflet, such as at the position midway between the commissure points AC and PC near the leaflet/annulus junction, in order to advance the "extra" arm (i.e., arm 94c) underneath the posterior leaflet. The posterior leaflet would then have two anchors—one starting at the AC commissure and one starting at the middle of the posterior leaflet (i.e., in the so-called "P2" section). Such a configuration may provide improved deployment and anchoring capabilities.

Figure 13:
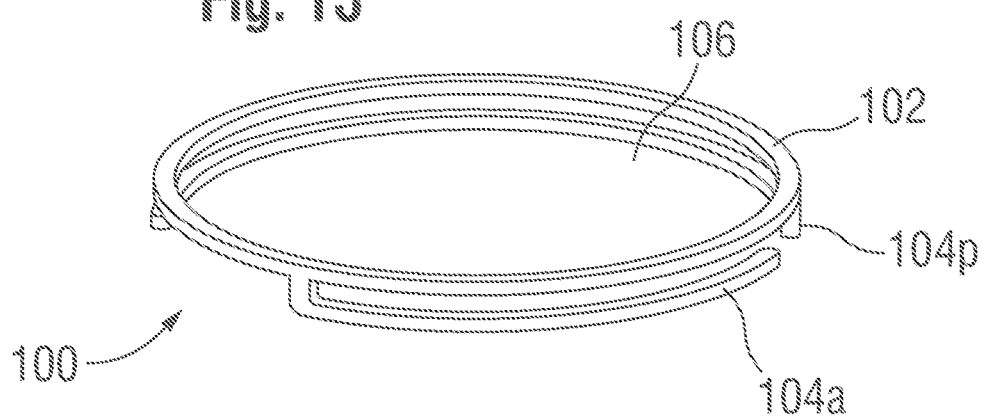
FIG. 13 is a perspective view of a device according to an embodiment of the invention.

A further embodiment of the invention is depicted in FIG. 13, wherein an anchor assembly 100 has a central portion 102 with anchors 104a, 104p positioned below (e.g., downstream of) the central portion 102. This configuration provides the potential for having a larger central opening 106 on the central portion 102 for a given native valve annulus size, which could thus accommodate a larger prosthetic valve orifice (where the anchor assembly is part of a prosthetic valve assembly) or a larger native valve orifice (where the anchor assembly is part of a repair device such as an annuloplasty ring).

Figure 14A:
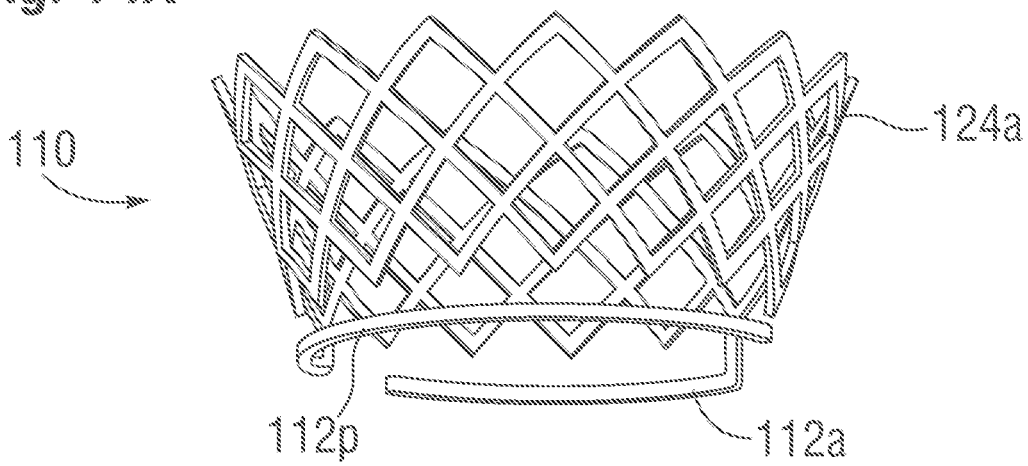
FIGS. 14A-14B are perspective views of devices according to embodiments of the invention.
Figure 14B:
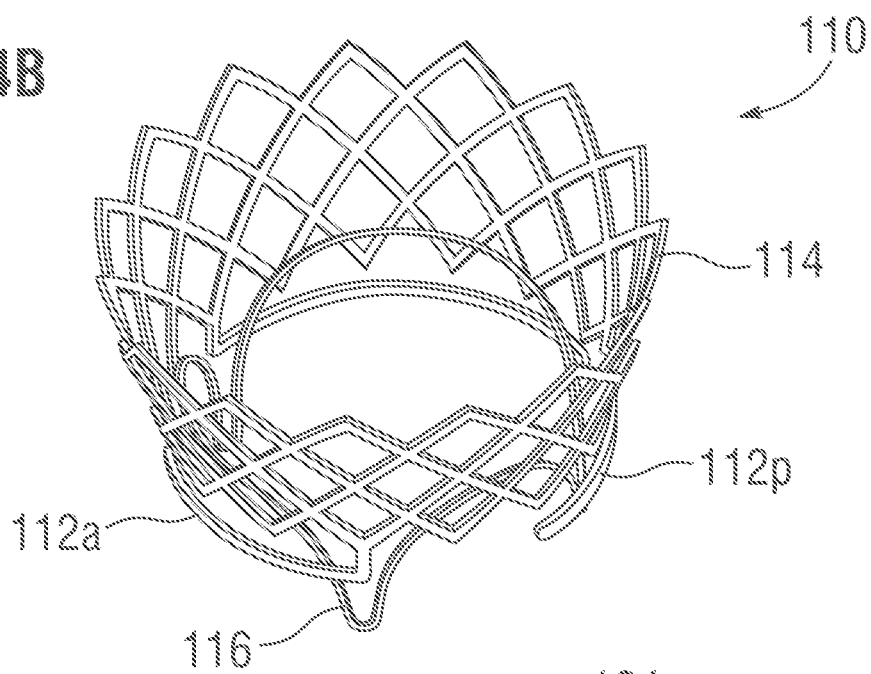

FIGS. 14A and 14B depict further embodiments of an anchor assembly 110, wherein anchors 112a, 112p are secured directly to a central portion in the form of a stent structure 114. The stent structure 114 is thus the central portion in lieu of a central ring portion such as depicted in FIG. 3. FIG. 14B has the addition of the valve support assembly (i.e., commissure supports 116) being formed with or otherwise attached to the assembly 110. Such anchor assemblies could be useful as part of a prosthetic valve assembly, such as that previously depicted in FIGS. 7A-7D. The embodiments of FIGS. 14A-14B have the additional advantage that the entire anchor assembly can be radially compressed, so that a prosthesis (e.g., annuloplasty ring and/or prosthetic heart valve) could be crimped or otherwise radially compressed into a smaller delivery profile for potential delivery to and deployment at the native annulus via catheterization (e.g., percutaneous/MIS). The device as shown in FIGS. 14A-14B could be delivered through a catheter in a percutaneous or minimally-invasive type intervention, or via open heart.

Figure 15:
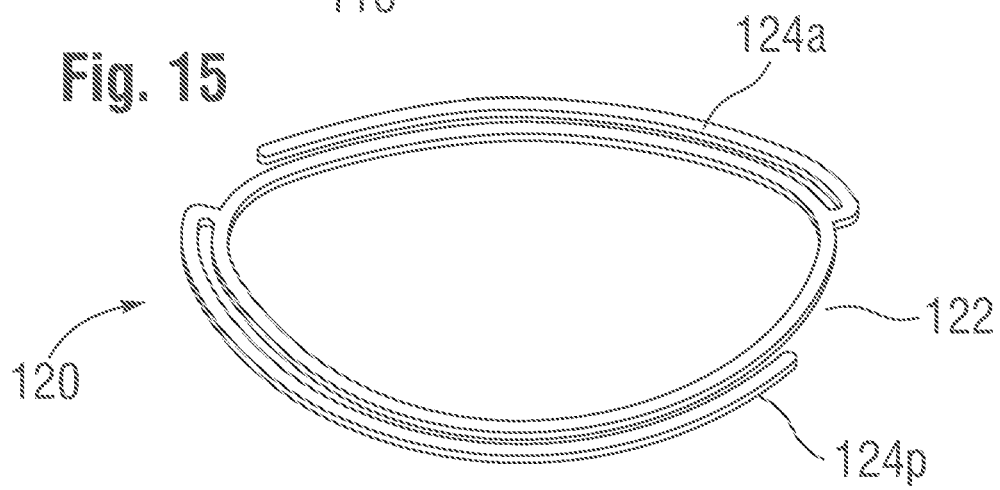
FIG. 15 is a top view of a device according to an embodiment of the invention.

Although the embodiments depicted above generally had substantially circular configurations, which may be preferred in some applications such as prosthetic heart valves and annuloplasty rings, the invention is not so limited. For example, non-circular configurations could also be used, such as the generally D-shaped configuration depicted in FIG. 15. The anchor assembly 120 has a central portion 122 which is substantially D-shaped, with anchors 124a, 124p extending therefrom and curving to match the substantially D-shape of the central portion 122. Such non-circular configurations could be particularly useful where the anchor assembly 120 was serving as part of an annuloplasty ring or similar repair device, such as an annuloplasty ring for the mitral valve. Note that an anchor assembly according to the invention, whether circular or non-circular, does not have to be planar. For example, three-dimensional forms, such as a so-called "3D saddle shape" like that disclosed in U.S. Pat. No. 6,805,710, issued Oct. 19, 2004 and entitled "Mitral Valve Annuloplasty Ring for Molding Left Ventricle Geometry" (the entire contents of which are incorporated by reference herein) could also be used with the invention in order to form a device to conform to, or to deform/reshape, the native anatomy.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims.

What is claimed is:

1. A method of implanting a prosthetic implant at a native valve annulus having resident valve leaflets, comprising:
providing a prosthetic implant comprising an anchoring device having two ring portions each having an associated anchor extending therefrom, the ring portions each being rotatable with respect to each other, each of the anchors having a proximal fixed end secured to an associated ring portion and terminating in a distal free end not connected to the associated ring portion, wherein each of the anchors is spaced slightly away from and runs in a continuous, unbroken fashion substantially parallel to a circumference of the associated ring portion so as to form a valve leaflet-receiving slot between the anchor and the associated ring portion;
positioning the anchoring device with the anchors adjacent the native valve annulus, with a fluid flow axis of the prosthetic implant generally parallel to a fluid flow path through the native valve annulus; and
independently rotating each of the ring portions to advance the distal free ends of each anchor underneath a resident valve leaflet thereby slidingly advancing the resident valve leaflets into the leaflet-receiving slots.

2. The method of claim 1, wherein the prosthetic implant comprises a prosthetic heart valve having a support frame and leaflets with the leaflets secured to the support frame to form a one-way valve structure controlling fluid flow along the flow axis, and, wherein the anchoring device is secured to the support frame.

3. The method of claim 1, wherein each anchor lies in the same plane as and radially outward from the associated ring portion.

4. The method of claim 1, wherein each anchor lies in a different plane than and axially spaced from the associated ring portion.

5. The method of claim 1, wherein in an anchored configuration the proximal fixed ends of the anchors are spaced at least about 120 degrees apart.

6. The method of claim 1, wherein the anchoring device has two anchors, one on each ring portion, and one anchor is longer than the other.

7. The method of claim 1, further comprising a cloth covering around each of the anchors.

8. A method, comprising:
providing an anchoring device having two ring portions each having an associated anchor extending therefrom, the ring portions each being rotatable with respect to each other, each of the anchors having a proximal fixed end secured to an associated ring portion and terminating in a distal free end not connected to the associated ring portion, wherein each of the anchors runs along a circumference of the associated ring portion so as to form a valve leaflet-receiving area between the anchor and the associated ring portion;
positioning the anchoring device with the anchors proximate a native valve annulus; and
rotating one of the two ring portions to slidingly advance a native valve leaflet into the leaflet-receiving area associated therewith.

9. The method of claim 8, further comprising independently rotating another of the two ring portions to slidingly advance another native valve leaflet into the leaflet-receiving area associated therewith.

10. The method of claim 8, wherein the anchoring device has a prosthetic heart valve secured therein, the prosthetic heart valve having a support frame and leaflets with the leaflets secured to the support frame to form a one-way valve structure controlling fluid flow along the flow axis.

11. The method of claim 8, wherein each anchor lies in the same plane as and radially outward from the associated ring portion.

12. The method of claim 8, wherein each anchor lies in a different plane than and axially spaced from the associated ring portion.

13. The method of claim 8, wherein the anchoring device has two anchors, one on each ring portion, and one anchor is longer than the other.

14. The method of claim 8, further comprising a cloth covering around each of the anchors.

15. A method, comprising:
providing an anchoring device having a first ring portion having a first anchor extending therefrom and a second ring portion having a second anchor extending therefrom, the first ring portion being rotatable relative to the second ring portion, wherein the first anchor has a first fixed end secured to the first ring portion and terminates at a first free end and forms a first valve leaflet-receiving area between the first anchor and the first ring portion, and the second anchor has a second fixed end secured to the second ring portion and terminates at a second free end and forms a second valve leaflet-receiving area between the second anchor and the second ring portion;

positioning the anchoring device proximate a native valve annulus; and rotating the first ring portion such that a first native valve leaflet enters the first leaflet-receiving area.

16. The method of claim 15, further comprising rotating the second ring portion such that a second native valve leaflet enters the second leaflet-receiving area.

17. The method of claim 15, wherein the anchoring device has a prosthetic heart valve secured therein, the prosthetic heart valve having a support frame and leaflets with the leaflets secured to the support frame to form a one-way valve structure controlling fluid flow along the flow axis.

18. The method of claim 15, wherein the first anchor and the second anchor each lie in the same plane.

19. The method of claim 15, wherein the first anchor and the second anchor each lie in a different plane.

20. The method of claim 15, further comprising securing a prosthetic heart valve inside of the anchoring device.

* * * * *